United States Patent
Martin et al.

(10) Patent No.: US 6,697,739 B2
(45) Date of Patent: Feb. 24, 2004

(54) TEST FOR LINKAGE AND ASSOCIATION IN GENERAL PEDIGREES: THE PEDIGREE DISEQUILIBRIUM TEST

(75) Inventors: Eden R. Martin, Hillsborough, NC (US); Norman L. Kaplan, Chapel Hill, NC (US)

(73) Assignees: Duke University, Durham, NC (US); The United States of America as represented by the Department of Health and Human Services, Washington, DC (US)

( * ) Notice: Subject to any disclaimer, the term of this patent is extended or adjusted under 35 U.S.C. 154(b) by 375 days.

(21) Appl. No.: 09/767,453

(22) Filed: Jan. 23, 2001

(65) Prior Publication Data

US 2002/0055821 A1 May 9, 2002

Related U.S. Application Data

(60) Provisional application No. 60/327,560, filed on Aug. 4, 2000.

(51) Int. Cl.$^7$ .............................................. G06F 17/00
(52) U.S. Cl. ......................................................... 702/19
(58) Field of Search ............................ 435/6; 436/63; 702/19

(56) References Cited

PUBLICATIONS

Abstract, Martin, E. R., et al., *A weighted sibship disequilibrium test for linkage and association in discordant sibships*, No. 2462.

Abstract, Wilson, A.F., et al., *The Genometric Analysis Simulation Program (G.A.S.P.): a software tool for testing and investigating methods in statistical genetics*, Am. of Hum. Gnet., vol. 59, p. A193 (1996).

Boehnke, Michael, et al., *Genetic Association Mapping Based on Discordant Sib Pairs: The Discordant–Alleles Test*, Am. J. Hum. Genet., vol. 62, pp. 950–961 (1998).

Curtis, D., et al., *A Note on the Application of the Transmission Disequilibrium Test When a Parent Is Missing*, Am. J. Hum. Genet., vol. 56, pp. 811–812 (1995).

Curtis, D., *Use of siblings as controls in case–control association studies*, Ann. Hum. Genet., vol. 61, pp. 319–333 (1997).

Horvath, Steve, et al., *A Discordant–Sibship Test for Disequilibrium and Linkage: No Need for Parental Data*, Am. J. Hum. Genet., vol. 63, pp. 1886–1897 (1998).

Knapp, Michael *The Transmissioni/Disequilibrium Test and Parental–Genotype Reconstruction: The Reconstruction––Combined Transmission/Disequilibrium Test*, Am. J. Hum. Genet., vol. 64, pp. 861–870 (199).

Martin, E.R., et al., *Tests for Linkage and Association in Nuclear Families*, Am. J. Hum. Genet., vol. 61, pp. 439–448 (1997).

Monks, S.A., et al., *A Comparative Study of Sibship Tests of Linkage and/or Association*, Am. J. Hum. Genet., vol. 63, pp. 1507–1516 (1998).

Monks, S.A., et al., *Removing the Sampling Restrictions from Family–Based Tests of Association for a Quantitative–Trait Locus*, Am. J. Hum. Genet., vol. 66, pp. 576–592 (2000).

Spielman, Richard S., et al., *A Sibship Test for Linkage in the Presence of Association: The Sib Transmission/Disequilibrium Test*, Am. J. Hum. Genet., vol. 62, pp. 450–458 (1998).

Spielman, Richard S., et al., *The TDT and Other Family––Based Tests for Linkage Disequilibrium and Association*, Am. J. Hum. Genet., vol. 59, pp. 983–989 (1996).

Spielman, Richard S., et al., *Transmission Test for Linkage Disequilibrium: The Insulin Gene Region and Insulin–dependent Diabetes Mellitus (IDDM)*, Am. J. Hum. Genet., vol. 52, pp. 506–516 (1993).

Primary Examiner—James Martinell
(74) Attorney, Agent, or Firm—Myers Bigel Sibley & Sajovec (57) ABSTRACT

The present invention provides a method for the analysis of linkage disequilibrium between at least one marker locus and a disease or trait locus of interest. The method comprises the steps of: (a) providing a data set comprising a marker locus with at least two alleles for a plurality of extended pedigrees (e.g., plant pedigrees, animal pedigrees), where N is the number of unrelated extended pedigrees, at least one of said extended pedigrees containing at least one informative nuclear family or informative discordant sibship; then (b) determining a random variable $X_T$ for each triad within an informative nuclear family for each allele $M_i$; (c) determining a random variable $X_S$ for each DSP within an informative discordant sibship for each allele $M_i$; (d) determining a summary random variable D from $X_S$ and $X_T$ for each of said extended pedigrees for each allele $M_i$; and then (e) determining a statistic T from each of said summary random variables D from each of said N unrelated extended pedigrees for each allele $M_i$. An extreme (large or small) value for T indicates greater linkage disequilibrium.

44 Claims, 3 Drawing Sheets

Provide a data set comprising a marker locus with at least two alleles for a plurality of extended pedigrees, where N is the number of unrelated extended pedigrees, at least one of the extended pedigrees containing at least one informative nuclear family or informative discordant sibship. 11

Determine a random variable $X_T$ for each triad within an informative nuclear family for each allele $M_i$. 12

Determine a random variable $X_S$ for each DSP within an informative discordant sibship for each allele $M_i$. 13

Determine a summary random variable D from $X_S$ and $X_T$ for each of the extended pedigrees for each allele $M_i$. 14

Determine a statistic T from each of the summary random variable D from each of said N unrelated extended pedigrees for each allele $M_i$, an extreme value for T indicating greater linkage disequilibrium. 15.

Figure 1

Structure of Extended Pedigrees Used in Simulations

TEST FOR LINKAGE AND ASSOCIATION IN GENERAL PEDIGREES: THE PEDIGREE DISEQUILIBRIUM TEST

RELATED APPLICATIONS

This application is a continuation-in-part of commonly owned, application Ser. No. 60/327,560 filed Aug. 4, 2000 now abandoned, which is a conversion from Ser. No. 09/632,700, filed on Aug. 4, 2000, the disclosure of which is incorporated by reference herein in its entirety.

STATEMENT OF GOVERNMENT SUPPORT

This invention was made with government support under grant numbers 1RO1 NS32830-05 and 1PSO NS3837101. The government has certain rights to this invention.

FIELD OF THE INVENTION

The present invention concerns methods, particularly computer-based methods, along with corresponding systems and computer code products for use in conducting linkage disequilibrium studies on pedigrees containing multiple nuclear families and/or discordant sibships.

BACKGROUND OF THE INVENTION

Family-based tests for linkage and allelic association, i.e., linkage disequilibrium, have received a great deal of attention in the past several years. The transmission/disequilibrium test (TDT) was proposed to test for linkage disequilibrium in family triads, containing two parents and an affected offspring (R. Spielman et al., *Am. J. Hum. Genet.* 52, 506–516 (1993)). The TDT was extended to allow for multiple affected offspring while remaining a valid test of linkage disequilibrium (E. Martin et al., *Am. J. Hum. Genet.* 61, 439–448 (1997)). For late onset diseases for which parents may not be available, a battery of tests using phenotypically discordant sib pairs has been proposed (D. Curtis, *Ann. Hum. Genet.* 61, 319–333 (1977); R. Spielman and W. Ewens, *Am. J. Hum. Genet.* 62, 450–458 (1998); M. Boehnke and C. Langefeld, *Am. J. Hum. Genet.* 62, 950–961 (1998)). Recently, the sibship disequilibrium test (SDT) was proposed to allow for the use of discordant sibships of larger size (S. Horvath and N. Laird, *Am. J. Hum. Genet.* 63, 1886–1897 (1998)). A limitation of these tests is that, while they remain valid tests of linkage, they are not valid tests of association if related nuclear families and/or sibships from larger pedigrees are used.

Accordingly, there remains a need for valid tests of linkage disequilibrium that employ related nuclear families and/or sibships from larger pedigrees.

SUMMARY OF THE INVENTION

Often data are available for larger pedigrees with multiple nuclear families and/or discordant sibships, and it would be desirable to have a valid test of linkage disequilibrium that can use all potentially informative data, even from extended pedigrees. With this goal, we have developed the Pedigree Disequilibrium Test (PDT) for analysis of linkage disequilibrium in general pedigrees. This test uses data from related nuclear families and discordant sibships from extended pedigrees. Furthermore, the test retains a key property of the TDT in that it is valid even when there is population substructure.

The difficulty with testing for association with related families, is that genotypes of related individuals are correlated if there is linkage, even if there is no allelic association in the population. Thus, it is incorrect to treat nuclear families or discordant sibships from extended pedigrees as independent when testing for association if there is linkage. An appropriate strategy is to base the test on a random variable measuring linkage disequilibrium for the entire pedigree rather than treating related nuclear families or sibships as if they were independent. A measure of linkage disequilibrium is defined for each triad and each discordant sib pair within a pedigree, and the average of the quantities is the measure of linkage disequilibrium for the pedigree. It is these random variables for independent pedigrees that form the basis of the PDT.

The present invention provides a method for the analysis of linkage disequilibrium between at least one marker locus and a disease or trait locus of interest. The method comprises the steps of:

(a) providing a data set comprising a marker locus with at least two alleles for a plurality of extended pedigrees (e.g., plant pedigrees, animal pedigrees), where N is the number of unrelated extended pedigrees, at least one of said extended pedigrees containing at least one informative nuclear family or informative discordant sibship; then (b) determining a random variable $X_T$ for each triad within a nuclear family or informative nuclear family for each allele $M_i$;

(c) determining a random variable $X_S$ for each DSP within a discordant sibship or informative discordant sibship for each allele $M_i$;

(d) determining a summary random variable D from $X_S$ and $X_T$ for each of said extended pedigrees for each allele $M_i$, and then;

(e) determining a statistic T from each of said summary random variables D from each of said N unrelated extended pedigrees for each allele $M_i$ an extreme value for T indicating greater linkage disequilibrium.

A variety of different types of data can be accommodated. For example, each of said extended pedigrees can contain at least one nuclear family; each of said extended pedigrees can contain at least one discordant sibship; each of said extended pedigrees containing at least one nuclear family and at least one informative discordant sibship; etc.

In a particular embodiment, the step (b) of determining a random variable $X_T$ for each triad within a nuclear family for each allele $M_i$ is carried out according to the formula:

$$X_T = (\text{Number } M_i \text{ transmitted} - \text{Number of } M_i \text{ not transmitted}).$$

In a particular embodiment, said step (c) of determining a random variable $X_S$ for each DSP within an informative discordant sibship for each allele $M_i$ is carried out according to the formula:

$$X_S = (\text{Number } M_i \text{ in affected sib} - \text{Number of } M_i \text{ in unaffected sib}).$$

In a particular embodiment, each of the extended pedigrees contains $n_T$ triads from informative nuclear families and $n_S$ DSPs from informative discordant sibships, and the step (d) of determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right]$$

In a particular embodiment, the step (e) of determining a statistic T from each of said summary random variables D from each of said N unrelated extended pedigrees for each allele $M_i$ is carried out according to formula (1):

$$T = \frac{\sum_{i=1}^{N} D_i}{\sqrt{\sum_{i=1}^{N} D_i^2}} \quad (1)$$

wherein T is a disequilibrium statistic for allele $M_i$, an extreme value for T indicating greater linkage disequilibrium.

In a particular embodiment, the method further comprises the step of: (f) determining a global statistic T' from each statistic T for each allele $M_i$, an extreme value for T' indicating greater linkage disequilibrium.

A particular embodiment of the PDT procedure described above is referred to herein as the "PDT-Sum" statistic. In this, each of the extended pedigrees contains $n_T$ triads from informative nuclear families and $n_S$ DSPs from informative discordant sibships, and the step (d) of determining a summary random variable D from $X_S$ and $X_T$ for each of said extended pedigrees for each allele $M_i$ is carried out according to the formula:

$$D = \sum_{j=1}^{n_T} X_{Tj} + \sum_{j=1}^{n_S} X_{Sj}$$

The $n_T$ triads from informative nuclear families and $n_S$ DSPs from informative discordant sibships are selected based upon genotype as described herein or on a criteria other than genotype as described below.

Another particular embodiment of the PDT procedure is referred to as the "PDT-Average" procedure herein. In this, each of the extended pedigrees contains $n_T$ triads from nuclear families and $n_S$ DSPs from discordant sibships, and the step (d) of determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right]$$

However, in the PDT average procedure, the $n_T$ triads from nuclear families and $n_S$ DSPs from discordant sibships are selected based upon a criteria other than genotype (including, but not limited to, criteria such as age, gender, clinical characteristic, phenotype, and random (that is, randomly chosen)). As will be appreciated, using all, or the total number, of nuclear families and discordant sibships is necessarily a selection based upon a criteria other than genotype.

The foregoing and other objects and aspects of the present invention are explained in greater detail in the drawings herein and the specification set forth below.

DETAILED DESCRIPTION OF THE PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As will be appreciated by one of skill in the art, the present invention may be embodied as a method, data processing system, or computer program product. Accordingly, the present invention may take the form of an entirely hardware embodiment, an entirely software embodiment, or an embodiment combining software and hardware aspects. Furthermore, the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices.

The present invention is described below with reference to flowchart illustrations of methods, apparatus (systems), and computer program products according to an embodiment of the invention. It will be understood that each block of the flowchart illustrations, and combinations of blocks in the flowchart illustrations, can be implemented by computer program instructions (or code means). These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

In the following sections, we describe the statistic for the PDT. We use computer simulations to demonstrate validity of the test when the asymptotic distribution is used to assess the significance of the test. We then compare the power of the PDT to the alternative of sampling a single nuclear family or discordant sibship from the pedigrees and applying existing methods. Finally, we examine issues such as robustness of normal approximation to small samples and effect of misclassification of unaffected siblings on power.

The following terms and phrases are used herein:

Marker locus—A region of DNA having different forms (alleles) segregating in the population that can be scored through molecular methods.

Trait or disease locus—A region of DNA having different forms segregating in the population in a manner corresponding to individuals affected or unaffected with a particular trait or disease.

Trait or disease as used herein includes any phenotype or disease, including risk of developing such trait or disease, and including both physical and behavioral traits and diseases. Examples include, but are not limited to, high blood pressure, cigarette smoking, asthma, cardiovascular disease (e.g., myocardial infarction, arrhythmia, etc.), cancer (e.g., breast cancer, prostate cancer, colon cancer, lung cancer, ovarian cancer, etc.), arthritis (including rheumatoid arthritis and osteoarthritis), Alzheimer's disease, Parkinson's disease, etc.

Linkage disequilibrium—A statistical association between alleles at different loci (for example, alleles at a marker locus and a putative trait or disease locus.

Extended pedigree—A family that includes relatives outside of the nuclear family.

Informative nuclear family—A family with at least one affected offspring, with both parents genotyped, and with at least one parent heterozygous for the marker locus.

Informative discordant sibship—A family with at least one affected and unaffected sibling with different marker genotypes. Parents may or may not be alive Triad—A family with one affected offspring and preferably two living parents.

DSP—A pair of siblings with one affected and one unaffected.

Extreme value—A value of the statistic (e.g., T) that is sufficiently great or small (positive or negative) to avoid a false positive association between the marker locus and the trait or disease locus, at the desired significance level of the test (e.g. p<0.1, p<0.05, or p<0.01.).

Figure 1:
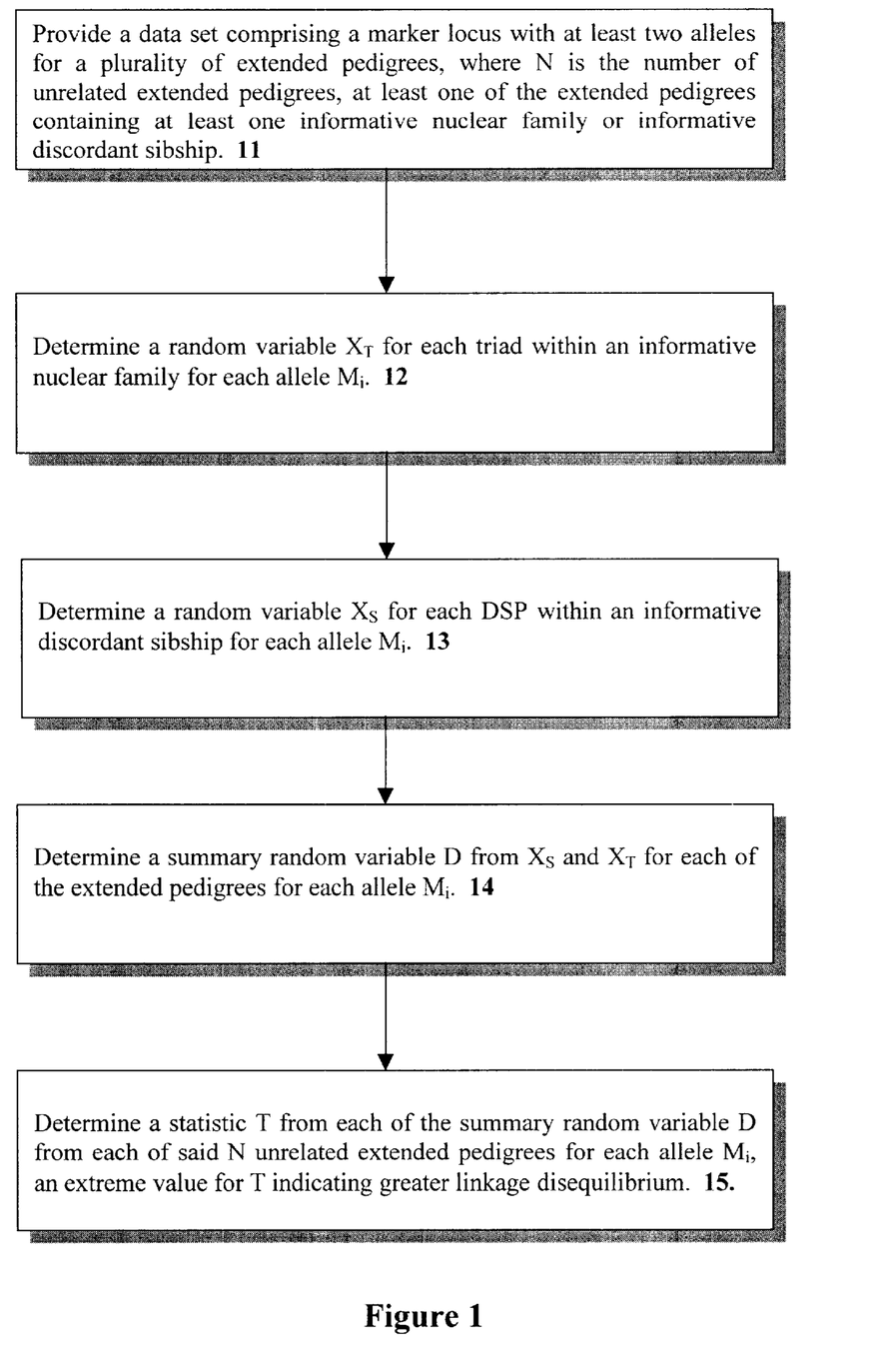
FIG. 1 is a flow chart or block diagram that illustrates systems, method and/or computer program products of embodiments of the present invention.

The present invention is explained in overview in FIG. 1 and in greater detail below. As set forth in FIG. 1, the present invention involves, initially, providing a data set comprising a marker locus with at least two alleles for a plurality of extended pedigrees, where N is the number of unrelated extended pedigrees, at least one of (and typically a plurality of; e.g., 10, 20, 50, 100 or more) said extended pedigrees containing at least one informative nuclear family and/or informative discordant sibship 11. Note that extended pedigrees that do not contain either an informative nuclear family or an informative discordant sibship can be analyzed in the method along with extended pedigrees that do, but extended pedigrees that do not contain such features simply add no informational value to the ultimate statistic. A random variable $X_T$ is then determined for each triad within an informative nuclear family for each allele $M_i$ 12, and a random variable $X_S$ is determined for each DSP within an informative discordant sibship for each allele $M_i$ 13. Note that, while an order of determination is depicted in FIG. 1, no such order is required for steps 12 and 13. Next, a summary random variable D is determined 14 from $X_S$ and $X_T$ for each of said extended pedigrees for each allele $M_i$. Finally, a statistic T is determined 15 from each of the summary random variables D from each of said N unrelated extended pedigrees for each allele $M_i$ an extreme value (positive or negative) for T indicating greater linkage disequilibrium. Each of the steps or features set forth in FIG. 1 is explained in greater detail below.

1. Methods

While the present invention is concerned primarily with the analysis of human pedigrees, the invention may be carried out with any animal species, particularly mammalian species such as dogs, cats, horses, cows, etc., for veterinary and animal husbandry purposes, with any plant species (e.g., vascular plants such as monocots and dicots), and in general may be carried out with any type of organism that propagates by mating between two individuals.

Test Statistic. There are two types of families that may give information about linkage disequilibrium. Informative nuclear families are ones in which there is at least one affected child, both parents genotyped at the marker and at least one parent heterozygous. Informative discordant sibships have at least one affected and unaffected sibling (DSP) with different marker genotypes and may or may not have parental genotype data. Informative extended pedigrees contain at least one informative nuclear family and/or discordant sibship.

Consider a marker locus with two alleles, $M_1$ and $M_2$. For any family triad, there is a pair of alleles that has been transmitted to the affected child and a pair of alleles that has not been transmitted. Define a random variable for each triad within an informative nuclear family:

$$X_T = (\#M_1 \text{ transmitted}) - (\#M_1 \text{ not transmitted})$$

Similarly, define a random variable for each DSP within an informative discordant sibship:

$$X_S = (\#M_1 \text{ in affected sib}) - (\#M_1 \text{ in unaffected sib})$$

Finally, for a pedigree containing $n_T$ triads from informative nuclear families and $n_S$ DSPs from informative discordant sibships, define a summary random variable:

$$D = \frac{1}{n_T + n_S}\left[\sum_{j=1}^{n_T} X_{Tj} + \sum_{j=1}^{n_S} X_{Sj}\right]$$

Note that all possible triads from informative nuclear families and all possible DSPs from informative discordant sibships from the pedigree are included in the average. Under the null hypothesis of no linkage disequilibrium, $E(X_T)=0$ for all triads and $E(X_S)=0$ for all DSPs and, consequently, $E(D)=0$ for any pedigree. If N is the total number of unrelated informative pedigrees in the sample and $D_i$ is the summary random variable for the ith pedigree, then, under the null hypothesis of no linkage disequilibrium, $$E\left(\sum_{i=1}^{N} D_i\right) = 0 \text{ and}$$

-continued $$Var\left(\sum_{i=1}^{N} D_i\right) = \sum_{i=1}^{N} Var(D_i)$$

$$= E\left(\sum_{i=1}^{N} D_i^2\right)$$

Hence, we would expect the statistic $$T = \frac{\sum_{i=1}^{N} D_i}{\sqrt{\sum_{i=1}^{N} D_i^2}} \qquad (1)$$

to be asymptotically normal with mean 0 and variance 1 under the null hypothesis of no linkage disequilibrium. The PDT is based on this statistic, T.

Relationship to TDT and Sib-TDT. There are several cases that deserve mention. Suppose that the data consist of only independent family triads. In this case, the TDT can be used as to test for linkage disequilibrium (R. Spielman et al., *Am. J. Hum. Genet.* 52, 506–516 (1993)). The TDT differs from the PDT in that it treats the contribution from heterozygous parents as independent. For the PDT, the triads are the independent units. It is of interest to know how these two tests compare in a sample of family triads.

For a biallelic marker locus, define a random variable for each heterozygous parent of an affected child, $Y_i = (\#M_1 \text{ transmitted}) - (\#M_1 \text{ not transmitted})$ for i=1, . . . ,h heterozygous parents. The TDT statistic is $$TDT = \frac{\left(\sum_{i=1}^{h} Y_i\right)^2}{\sum_{i=1}^{h} Y_i^2}$$

The numerators of the TDT statistic and $T^2$ (from equation 1) are the same, but the variance estimates in the denominators differ. Families with a single heterozygous parent contribute equally to both statistics, but variances are estimated differently for families with two heterozygous parents. In particular, $$\sum_{i=1}^{h} Y_i^2 = h$$

$$\sum_{i=1}^{N} D_i^2 = h + 2(n_c - n_d)$$

where $n_c$ is the number of times that two heterozygous parents in a triad transmit the same allele to the affected child; i.e., the number of concordant transmissions, and $n_d$ is the number of times that two heterozygous parents in a triad transmit different alleles to the affected child; i.e., the number of discordant transmissions. It follows that $$\frac{TDT}{T^2} = 1 + \frac{2(n_c - n_d)}{h}$$

Under the null hypothesis of no linkage or no association, $E(n_c - n_d) = 0$, thus the two tests are asymptotically equivalent under the null hypothesis.

Under the alternative hypothesis, when there is both linkage and association, the two tests are not necessarily equivalent. For example, suppose that the marker and disease alleles are in complete linkage disequilibrium, so tests are effectively conducted at the disease locus itself. Consider the case of a rare recessive disease locus and no phenocopies such that most affected children have two heterozygous parents and all transmissions are concordant for the disease allele. Then the TDT can be as much as 2 times the size of the PDT statistic, $T^2$, depending on the proportion of families with two heterozygous parents. For a dominant disease model with no phenocopies, families with two heterozygous parents have an affected child homozygous for the disease allele with probability ⅓ or heterozygous with probability ⅔. Thus, discordant transmissions are expected to occur twice as frequently as concordant transmissions, and the PDT statistic will be larger, on average, than the TDT statistic. We have constructed examples in which each test is more powerful than the other. However, in less extreme, and probably more realistic, examples there is likely to be little difference between the outcomes of the two tests.

The second case to consider is if the data consist of nuclear families with multiple affected offspring. The Tsp statistic is an extension of the TDT that allows for multiple affected children (E. Martin et al., *Am. J. Hum. Genet.* 61, 439–448 (1997)). Calculation of the Tsp statistic requires one to know whether a parent has transmitted the same or different marker alleles to each of their affected children. If both parents have the same heterozygous genotype and there is more than one affected child also having the same heterozygous genotype as the parents, then it is impossible to tell which parent transmitted which allele to each of those children. A strategy that leads to a conservative test is to assume, for these families, that each parent transmitted the same marker allele to each of the affected children having the same genotype as the parents, which provides an upper bound for the estimate of variance (Martin et al., 1997). These families cause no difficulty in the calculation of the PDT statistic, since there is no need to know the transmissions from an individual parent.

A third case that deserves mention is when the sample consists of independent discordant sib pairs. In this case, the PDT is the same as the Sib-TDT and the test of Curtis for a marker locus with two alleles (D. Curtis, *Ann. Hum. Genet.* 61, 319–333 (1997); R. Spielman and W. Ewens, *Am. J. Hum. Genet.* 62(2), 450–458 (1998)). For a sample of larger discordant sibships, the PDT is equivalent to the Weighted Sibship Disequilibrium Test (WSDT) (E. Martin et al., *Am. J. Hum. Genet.* 65(4), Supplement: A434 (1999)).

Population Substructure. One of the motivations behind the development of the original TDT, was the desire to have a test that is valid as a test of allelic association when there is population substructure. Consider a stratified population composed of two or more random mating subpopulations, in which there is no allelic association between marker and disease alleles in the subpopulations. However, there may be differences in disease prevalence and marker allele frequencies that lead to associations in the population at large if the substructure is ignored. The within-family nature of the TDT and the appropriate construction of the variance estimator guarantee that the TDT has the correct significance level provided there is no allelic association within the subpopulations. Similarly, the PDT is also valid as a test of association even if there is population stratification. To see that this is the case, consider the PDT statistic in (1). For any pedigree in the sample, $E(D_i)=0$ if there is no allelic association in any of the subpopulations. Thus, for a sample of N pedigrees from the population at large, $$E\left(\sum_{i=1}^{N} D_i\right) = 0.$$

The $$\text{Var}\left(\sum_{i=1}^{N} D_i\right)$$

can be partitioned into sum of the variances of sums of $D_i$ for each of the subpopulations, and each variance is estimated by the sum of squared values for $D_i$ for pedigrees in the subpopulation. Thus, as long as there is no allelic association (or no linkage) within each subpopulation, then the PDT statistic is asymptotically normal with mean 0 and variance 1.

Computer Simulations. We used computer simulations to examine the Type I error and power of the PDT. Simulations were conducted using the program G.A.S.P (A. Wilson et al., Am. J. of Hum. Genet. 59, A193 (1996)) to simulate marker and disease locus genotypes for pedigree members. Both marker and disease loci were assumed to be biallelic, and the loci were assumed to be in linkage equilibrium. Disease phenotypes were simulated based on disease locus genotypes according to a set of specified penetrances: $f_{11}, f_{12}$ and $f_{22}$, where $f_{ij}$ is the probability that an individual is affected with the disease, given that they carry genotype ij at the disease locus. We considered six genetic models, which are given in Table 1. For each model, we assumed that we were looking at a common disease polymorphism having frequency p=0.3. We considered two values for disease prevalence: 30% and 15%. For each value of prevalence, we varied the penetrances to vary the genetic effect; the gene will have the largest effect for models 1 and 4 and smallest for models 3 and 6. In all cases, the disease-locus alleles were assumed to act additively on the penetrance scale. A linked but unassociated marker locus with allele frequency q=0.3 was simulated for Type I error analyses. Since we are primarily interested in the properties of the test as a test for association in the presence of linkage, all simulations assumed 0 recombination between the marker and disease loci. Type I error tests used data from the marker locus, thus there is no allelic association. Power simulations used data from the disease locus itself, thus there is both complete linkage and association.

2. Results

The first issue that we examined, was how the PDT compares, in extended pedigrees, to standard methods which sample only a single nuclear family or discordant sibship from larger pedigrees to maintain validity as tests of linkage disequilibrium. In particular, we compared the Type I error and power of the PDT to the Sib-TDT (R. Spielman and W. Ewens, Am. J. Hum. Genet. 62(2), 450–458 (1998); D. Curtis, Ann. Hum. Genet. 61, 319–333 (1997)), the SDT (S. Horvath and N. Laird, Am. J. Hum. Genet. 63, 1886–1897 (1998)), and the Tsp test (E. Martin et al., Am. J. Hum. Genet. 61, 439–448 (1997)). The Sib-TDT uses only a single discordant sib pair from each pedigree. To improve power, the pair with maximally different genotypes was chosen for each pedigree (Curtis (1997)). The SDT uses data from informative discordant sibships, but only one sibship from each pedigree can be used to ensure validity as a test of association. For our simulations, a random informative discordant sibship was chosen from each pedigree. The Tsp test uses data from informative nuclear families with an arbitrary number of affected offspring. In extended pedigrees, only one nuclear family can be used in a test of linkage disequilibrium, so we selected a random informative nuclear family from each pedigree for analysis in our simulations. Note that when testing for association, the Tsp test is at least as powerful as the TDT, which can use only one affected offspring per family (Martin et al., (1997)). Therefore, we consider only the Tsp test for comparison with the PDT.

Figure 2:
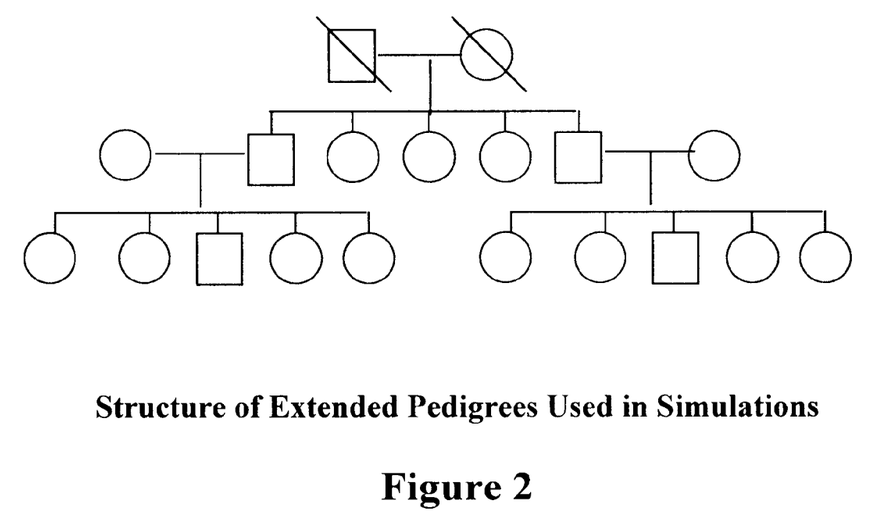
FIG. 2 illustrates the structure of extended pedigrees used in simulations carried out to demonstrate the present invention. Circles represent females; squares represent males; a slash through either symbol indicates the individual is deceased.

For each model, we simulated 5000 data sets each with 250 families with structure given in FIG. 2 (which is a non-limiting example family structure only). Pedigrees with three generations were simulated. Grandparental genotypes were scored as missing, but all other individuals were assumed to have genotypes and phenotypes known. Affection status of pedigree members was random conditional on disease genotype, thus the number of discordant sibships and nuclear families with affected children was variable. Type I error and power comparisons are shown in Table 2. In each case, the tests were conducted using the appropriate normal or chi-squared critical values for a test with nominal significance level 0.05. A significance level of 0.05 was used in our simulations merely for convenience. In practice, a more stringent significance level may be desired, particularly when tests are conducted at multiple marker loci. Based on 5000 repetitions, the approximate standard error for the estimate of Type I error is 0.003, assuming that the tests are estimating a Type I error close to 0.05. The standard errors for estimates of power depend on the true power being estimated, but for general reference an upper bound can be obtained by assuming a power of 0.5. For our simulations, this upper bound for standard error is 0.007.

The Type I error estimates are close to the nominal level for the Sib-TDT, SDT and PDT tests. However, the Tsp test is consistently conservative. This was expected since the Tsp test was constructed to be conservative to deal with ambiguity of transmissions from parents to multiple affected children, as was discussed previously. For the models with lower prevalence, the test is less conservative, which is the result of having fewer nuclear families with multiple affected children.

Power estimates in Table 2 show that the PDT is more powerful than the other tests for all of the models examined. For models 1, 2 and 3, the PDT is substantially more powerful than the other tests, with the greatest differences in powers being between the PDT and the SDT. For models 4, 5, and 6 the PDT was still more powerful than the other tests, but the gains were less than in the higher-prevalence models. We show in Table 2, the average number of affected siblings in each pedigree from our simulations. As would be expected, the higher-prevalence models (1, 2 and 3) have, on average, more affected siblings in each pedigree than in the lower-prevalence models (4, 5 and 6), thus, there is more extended family data for the PDT to take advantage of.

While the prevalences used in our simulations are admittedly high for most diseases, they are not unrealistic for common diseases such as osteoarthritis and cardiovascular disease among older individuals. Using high prevalence allows us to model a common susceptibility allele with low penetrance and a high phenocopy rate as is expected for complex diseases, while assuring that many families will contain multiple affected individuals. As demonstrated in Table 2, as prevalence decreases, the average number of affected individuals in each pedigree decreases and the power of the PDT becomes more similar to the other tests. Unless the recurrence risk to relatives is high or families are ascertained based on having multiple affecteds, one is unlikely to find multiple affected relatives in an extended pedigree for diseases with low prevalence, and consequently there will be less additional data for use in the PDT.

It makes sense that the PDT is more powerful than the other tests examined here in extended families when there are additional data for the PDT to use. However, it is not clear how the PDT compares to the other tests when there is not extended family data, but only independent nuclear families or sibships. Would we do well to use the PDT in this situation? To begin to examine this question, we simulated nuclear families with two and five siblings and parents. The data were analyzed with the Tsp test and the PDT using the parental transmission information. To address the case in which parental data are unavailable, we also analyzed the sib data with the Sib-TDT, SDT and PDT assuming that there were no parental data. Simulations were conducted under models 1 and 4, and are based on data sets of 500 nuclear families in each of 5000 replicates. All tests used the asymptotic approximations to assess significance, assuming a nominal significance level of 0.05.

Estimates of power for the different tests in nuclear families are shown in Table 3. The first two rows present the case for which there are only two siblings in each family. It can be seen that, in this case, if parental genotype data are available, the tests using the parental data in the Tsp test or PDT, gives higher power than the sib-based tests (SDT or Sib-TDT) or the PDT not using the parental data. Furthermore, with parental data, the Tsp test and PDT have comparable power. It is important to note that our previous simulations showed that generally the Tsp test will be conservative and may have lower Type I error than the PDT (Table 2), although for families with only two offspring, we found that Type I error is very close to the nominal level (data not shown). If parental genotype data are unavailable, then with two sibs per family, the PDT is equivalent to the Sib-TDT, and the SDT has comparable power. This case of two sibs per family is the case examined theoretically by Horvath and Laird (1998) in which they showed that the SDT and Sib-TDT often had similar powers with neither being uniformly more powerful than the other.

For families with five siblings, when parents are used, the estimate of power for the PDT is larger than for the Tsp test for model 1, but the estimate of powers for the two tests are similar for model 4. Again, it is important to keep in mind that the Tsp test is expected to have lower Type I error than the PDT, particularly when there are many families with multiple affected siblings. For example, in simulations of five siblings per family for model 1, we obtained an estimate of Type I error of about 0.034 for the Tsp test using a nominal level of 0.05. Thus, the lower power of the Tsp test compared to the PDT for model 1, with an average of about two affected siblings per family, may be the result of the Tsp test being conservative. For analyses not using parental data, the powers of the Sib-TDT and the SDT are similar, and the PDT is more powerful than both tests. It is not surprising that the Sib-TDT is less powerful when there are multiple sibs since it can only use a single discordant pair from a sibship. However, the SDT was specifically constructed to use multiple siblings. The SDT is based on the sign of the difference between the number of times a particular allele occurs in affected siblings and the number of times it occurs in unaffected siblings; however, using the sign of this difference alone may not capture all of the information. The PDT uses the magnitude as well as the sign, which can increase power. This has been noted previously for the WSDT, which is equivalent to the PDT in independent discordant sibships (E. Martin et al., (1999)). These results demonstrate that even if there are no extended pedigrees so that the same data are used in the different tests, it may still be preferable to use the PDT. Interestingly, for the larger sibships, it appears to make little difference in the power of the PDT if parental data are used or not, which suggests that if parents are unavailable, this can be compensated for by sampling large sibships. Similar observations have been made also for application of family-based tests to quantitative traits (S. Monks and N. Kaplan, *Am. J. Hum. Genet.* 66, 576–592 (2000)).

Type I error estimates for the PDT based on 250 extended pedigrees were all close to the nominal level (Table 2); however it is important to examine the validity of the test for smaller samples when the asymptotic distribution is assumed. This is particularly important for the PDT in extended pedigrees since the random variables, $D_i$, will not necessarily have the same variances if pedigrees have different structures. Thus, one might question the accuracy of the variance estimate used in the PDT statistic. To examine this, we simulated 10,000 data sets with N=250, 100, 50 and 25 families with structure given in FIG. 2 and using model 1. Recall that affection status is random conditional on disease locus genotype for our simulations, so the simulated pedigrees will have variable structure with regard to the number and relationships of informative nuclear families and discordant sibships.

Table 4 shows estimates of Type I error for the PDT and other tests using the asymptotic critical values for nominal significance level 0.05 for different sample sizes. It can be seen that the asymptotic approximations are quite robust, even for samples as small as 25 pedigrees. The exception is the Tsp test, which is conservative, even for large samples. For these simulations, there were about 4.5 affected sibs per pedigree on average, so there is potentially a fair amount of information in each pedigree. However, the independent units are the pedigrees, thus there are few independent observations that go into the statistic and the robustness is somewhat surprising. It is noteworthy that using the lower prevalence model (model 4) gave similar results, although the estimates of Type I error are somewhat smaller than the nominal level for small numbers of families (data not shown). This shows that even with only about three affected sibs per pedigree the asymptotic approximations work well, being only slightly conservative for small samples.

Because age of onset is variable, one runs the risk of misclassifying individuals as unaffecteds because they may later become affected. We conducted simulations to examine the impact of such misclassification on the power of the PDT and other tests considered here. Misclassification was introduced into our simulations by allowing affected individuals to be misclassified as unaffected with probability $\rho$. Misclassification was independent of genotype and has the effect of reducing the penetrances by a factor of $(1-\rho)$. Table 5 shows estimates of power for the PDT and other tests for models 1 and 4. Estimates were based on 5000 replicate data sets with extended pedigrees with the structure given in FIG. 2. The total number of pedigrees simulated for each model was chosen so that we would generate an average of 150 pedigrees having at least one affected sibling.

In Table 5, we see that all of the tests lose power as the rate of misclassification increases; however, the PDT remains more powerful than the other tests that we consider. It is important to notice that even the Tsp test, which does not use unaffected siblings, loses power when there is misclassification. Misclassification has two effects on the make-up of the samples that influence power. One effect is that, as misclassification increases, the number of affected individuals in our samples decreases. This results in fewer affected individuals per pedigree. The reduction in the number of affecteds causes power to decrease for all of the tests, including the Tsp test. Power decreases more rapidly for the higher prevalence model (model 1) than for the lower prevalence model (model 4) since the number of affected siblings per pedigree decreases more dramatically for the higher prevalence model. For example, the average number of affected siblings per pedigree decreases from 4.5 to 2.5 for model 1 and from 2.5 to 1.6 for model 4 as misclassification goes from $\rho$ of 0 to 0.5. The second effect of the misclassification is that some of the unaffecteds are actually misclassified affecteds, and hence, tests comparing genotypes of affected and unaffected siblings will be biased toward the null hypothesis. It is clear that substantial misclassification can have a serious impact on the power of family-based association tests, but our simulations demonstrate that even with misclassification, it is still desirable to use the PDT to take advantage of extended family data.

3. Discussion

The motivation for developing the PDT was that often extended pedigree data are available to us and it would be desirable to use all of that data in a test for marker disease association studies. While there are many good tests available for use in independent nuclear families, there has been little discussion of association testing in larger pedigrees. Standard tests require selection of a single nuclear family or discordant sibship from extended pedigrees. Clearly, this is less than optimal, since it discards data. Furthermore, results for a data set may vary due to the random selection of nuclear families or sibships for inclusion. The PDT is a test for linkage disequilibrium, which uses all of the informative data in pedigrees, regardless of their size.

Our intention was to provide a test to take advantage of the pedigree data that we may be collecting for use in other analyses, such as testing for linkage. We are not necessarily advocating the collection of large pedigrees for association studies. Though optimal family size is an important question, we have not addressed the issue of study design in this work. The choice between large and small families depends on many factors. Not only is relative statistical power a consideration, but factors such as ease in ascertainment, disease prevalence, age of onset, and other types of analyses to be conducted must be taken into account.

We demonstrated that when affecteds are misclassified as unaffecteds, the PDT and the other family-based tests of association examined here lose power. However, we found that the PDT still remains more powerful than the other tests when extended family data is available. There are steps that one can take to improve the chances that we are using true unaffecteds, for example, one could analyze only older unaffected individuals. The PDT is constructed to give equal weight to informative triads and discordant sib pairs. If misclassification of unaffecteds is a large concern for the disease under study, it may be wise to give a smaller weight to the discordant sib pairs than to triads. The PDT statistic is easily modified by using a weighted average of contributions of triads and discordant sib pairs within a pedigree.

Although, we did not address it here, it is possible that misclassification may go in the other direction, with unaffecteds being misclassified as affecteds. This might happen, for example, if different syndromes have similar symptoms making differentiating diagnoses difficult. It is expected that this type of misclassification would also lead to a loss of power, and the loss may be even greater since families are ascertained through affected individuals. Here again it may be possible to apply a weighting function to the PDT, giving lower weight to DSPs in which the diagnosis of the affected sibling is uncertain.

As it is constructed, the PDT gives larger weight to larger sibships and nuclear families within a pedigree. Nuclear families with more triads or discordant sibships with more DSPs contribute more to the summary random variable for the pedigree than smaller nuclear families or sibships within the pedigree. However, there is no adjustment in the PDT for different size pedigrees that may be used in the analysis. It may be desirable to give more weight to larger pedigrees containing more information in the calculation of the statistic. One possibility would be to base a test on the weighted average of the pedigree summary random variables where the weight for a pedigree is some increasing function of triads and DSPs contributed by that pedigree. Of course, if one believes that the underlying disease mechanism may be different in multiplex families with many affecteds than in families with smaller numbers of affecteds, then a stratified analysis among the large and small families may be in order.

While our simulations demonstrate that using the asymptotic approximations to evaluate significance is quite robust, it would be desirable to have a permutation procedure that allows us to derive empirical p-values when the appropriateness of asymptotic distributions may be in question. It is simple to see how one might permute the data to derive a test of linkage in larger pedigrees simply by randomly permuting which allele is transmitted from parents to children. However, it is not clear how to permute the data to simulate the null hypothesis of no allelic association. It is essential that a test of allelic association allow for the possibility that there is linkage; thus, the permutation procedure must correctly preserve correlations between transmissions of individuals within a pedigree. It is not clear whether a simple permutation procedure can be developed for this purpose in general pedigrees All of the simulations presented here considered a marker locus with two alleles. Such explorations are appropriate given the emphasis on developing single nucleotide polymorphisms for use in association studies. However, this does not mean that multiallelic markers will not be used as well. We propose two extensions of the PDT for use with multiallelic markers that are commonly used in multiallelic versions of related tests. The first is to consider each allele versus all of the others and calculate a value for the PDT statistic for each allele. Multiple testing will be an issue since a test is conducted for each allele, and this should be accounted for in assessing significance. Alternatively, one can construct a global test by summing the squared PDT statistics for each of the alleles and multiplying the sum by $(m-1)/m$, where m is the number of marker alleles. Arguments similar to those used for other multiallelic extensions can be used to show that this statistic is approximately chi-squared with m−1 degrees of freedom (R. Spielman and W. Ewens, *Am. J. Hum. Genet.* 59(5), 983–989 (1996); E. Martin et al., (1997); S. Monks et al., *Am. J. Hum. Genet.* 63(5), 1507–1516 (1998)). Simulations have shown that the approximation does provide a test with Type I error close to the nominal level (data not shown).

The PDT was constructed assuming that an informative family triad has genotype data available for both parents, with at least one heterozygous. For markers with multiple alleles, it may be possible to gain information from triads in which there is only a single heterozygous parent and the genotype of the other parent unknown. Curtis and Sham (*Am. J. Hum. Genet.* 56, 811–812 (1995)) showed for the TDT that using triads with only one heterozygous parent genotyped could lead to bias, resulting in an inflated Type I error rate. This same potential bias applies to the PDT. To avoid bias, Curtis and Sham (1995) suggested to use these triads in the TDT only when the affected offspring has a heterozygous genotype different from the parent. This rule could also be used with the PDT to gain extra information from triads with missing parental data. It may also be possible to implement the method proposed by Knapp (*Am. J. Hum. Genet.* 64, 861–870 (1999)) to make inference about missing parental data.

Additional features that may be added to the invention described herein include procedures for weighting the contribution of particular discordant sib pairs or triads according to some function, such as a function dependent on age of a subject. For example, since there may be uncertainty as to whether unaffected individuals will remain unaffected, discordant sib pairs in which the unaffected sib is very young may be down-weighted and discordant sib pairs in which the unaffected sib is older may be up-weighted. It may also be desirable to give more weight to the contribution of triads to the PDT statistic than is given to the discordant sib pairs to adjust for uncertainty in affection status of the unaffected sib.

In summary, the PDT provides a test for linkage disequilibrium that is valid in general pedigrees. It was our desire to develop a test that is similar in spirit to the original TDT. Like the TDT, the PDT is theoretically intuitive and not computationally demanding. The test does retain the properties of the original TDT and Sib-TDT, namely it is valid as a test of both linkage and association even when there is population stratification. Our simulations have shown that, when extended pedigree data are available, substantial gains in power can be attained by using the PDT rather than using existing methods that use only a subset of the data. In fact, our simulations suggest that there may be advantages to using the PDT even if the data consist of independent families without extended family information. Thus, the PDT provides a general test of linkage disequilibrium that can be widely applied to different data structures.

TABLE 1

Disease models for simulations: penetrances ($f_{11}$, $f_{12}$ and $f_{22}$) and disease prevalence.

| Model | $f_{11}$ | $f_{12}$ | $f_{22}$ | prevalence |
|---|---|---|---|---|
| 1 | 0.39 | 0.330 | 0.26 | 0.30 |
| 2 | 0.37 | 0.320 | 0.27 | 0.30 |
| 3 | 0.35 | 0.315 | 0.28 | 0.30 |

TABLE 1-continued

Disease models for simulations: penetrances ($f_{11}$, $f_{12}$ and $f_{22}$) and disease prevalence.

| Model | $f_{11}$ | $f_{12}$ | $f_{22}$ | prevalence |
|---|---|---|---|---|
| 4 | 0.22 | 0.170 | 0.12 | 0.15 |
| 5 | 0.20 | 0.165 | 0.13 | 0.15 |
| 6 | 0.17 | 0.155 | 0.14 | 0.15 |

TABLE 2

Estimates of Type I error and power for four different tests with nominal significance level 0.05 based on 5000 replicates of 250 extended pedigrees. The average number of affected siblings per pedigree is given for power calculations.

| | Affected sibs | Test | | | |
|---|---|---|---|---|---|
| Model | per pedigree | Sib-TDT[a] | Sib-TDT[b] | Tsp[b] | PDT |
| | | Type I Error | | | |
| 1 | | 0.0456 | 0.0482 | 0.0328 | 0.0566 |
| 2 | | 0.0508 | 0.0478 | 0.0318 | 0.0464 |
| 3 | | 0.0538 | 0.0480 | 0.0338 | 0.0480 |
| 4 | | 0.0534 | 0.0514 | 0.0416 | 0.0490 |
| 5 | | 0.0494 | 0.0474 | 0.0424 | 0.0478 |
| 6 | | 0.0570 | 0.0496 | 0.0404 | 0.0510 |
| | | Power | | | |
| 1 | 4.5 | 0.6626 | 0.4814 | 0.6042 | 0.9064 |
| 2 | 4.5 | 0.4348 | 0.2816 | 0.3788 | 0.6764 |
| 3 | 4.5 | 0.2408 | 0.1600 | 0.1972 | 0.3960 |
| 4 | 2.5 | 0.7538 | 0.6240 | 0.7264 | 0.8996 |
| 5 | 2.5 | 0.4480 | 0.3420 | 0.4270 | 0.5944 |
| 6 | 2.5 | 0.1172 | 0.1018 | 0.1198 | 0.1616 |

[a]Sampling most genotypically different DSP from each pedigree
[b]Sampling a single nuclear family/sibship randomly from each pedigree

TABLE 3

Estimates of power for different tests with nominal significance level 0.05 based on 5000 replicates of 500 nuclear families having 2 and 5 offspring using models 1 and 4. Analysis conducted with and without parental genotype information. The average number of affected siblings per pedigree is indicated for each model.

| Number of sibs | Model | Affected sibs per pedigree | With parents | | Without parents | | |
|---|---|---|---|---|---|---|---|
| | | | Tsp | PDT | Sib-TDT[a] | SDT | PDT |
| 2 | 1 | 1.2 | 0.3988 | 0.3858 | 0.3032 | 0.3000 | 0.3032 |
| | 4 | 1.1 | 0.4412 | 0.4398 | 0.2844 | 0.2798 | 0.2844 |

TABLE 3-continued

Estimates of power for different tests with nominal significance level 0.05 based on 5000 replicates of 500 nuclear families having 2 and 5 offspring using models 1 and 4. Analysis conducted with and without parental genotype information. The average number of affected siblings per pedigree is indicated for each model.

| Number of sibs | Model | Affected sibs per pedigree | With parents | | Without parents | | |
|---|---|---|---|---|---|---|---|
| | | | Tsp | PDT | Sib-TDT[a] | SDT | PDT |
| 5 | 1 | 1.8 | 0.7462 | 0.8134 | 0.6730 | 0.7054 | 0.8294 |
| | 4 | 1.4 | 0.7926 | 0.7920 | 0.6948 | 0.6986 | 0.7820 |

[a]Sampling most genotypically different DSP from each pedigree

TABLE 4

Estimates of Type I for four different tests with nominal significance level 0.05 based on 10,000 replicates of N = 25, 50, 100 and 250 extended pedigrees

| | Test | | | |
|---|---|---|---|---|
| N | Sib-TDT[a] | SDT[b] | Tsp[b] | PDT |
| 25 | 0.0477 | 0.0498 | 0.0344 | 0.0490 |
| 50 | 0.0517 | 0.0504 | 0.0356 | 0.0500 |
| 100 | 0.0504 | 0.0516 | 0.0300 | 0.0488 |
| 250 | 0.0556 | 0.0485 | 0.0338 | 0.0512 |

[a]Sampling most genotypically different DSP from each pedigree
[b]Sampling a single nuclear family/sibship randomly from each pedigree

TABLE 5

Estimates of power for four tests allowing for misclassification of affecteds as unaffecteds with probability ρ. Nominal significance level is 0.05, and estimates are based on 5000 replicates with an average of 150 extended pedigrees with at least on affected sibling. The average number of affected siblings per pedigree is indicated for each model.

| Model | ρ | Affected sibs per pedigree | Test | | | |
|---|---|---|---|---|---|---|
| | | | Sib-TDT[a] | SDT[b] | Tsp[b] | PDT |
| 1 | 0 | 4.5 | 0.4526 | 0.3058 | 0.3828 | 0.7088 |
| | 0.1 | 4.1 | 0.4078 | 0.2872 | 0.3654 | 0.6480 |
| | 0.3 | 3.3 | 0.3424 | 0.2724 | 0.3236 | 0.5296 |
| | 0.5 | 2.5 | 0.2948 | 0.2314 | 0.2674 | 0.4134 |
| 4 | 0 | 2.5 | 0.5718 | 0.4528 | 0.5406 | 0.7438 |
| | 0.1 | 2.3 | 0.5384 | 0.4290 | 0.5026 | 0.6848 |
| | 0.3 | 2.0 | 0.4978 | 0.4132 | 0.4520 | 0.6164 |
| | 0.5 | 1.6 | 0.4622 | 0.4024 | 0.4174 | 0.5634 |

[a]Sampling most genotypically different DSP from each pedigree
[b]Sampling a single nuclear family/sibship randomly from each pedigree 4. Weighting Pedigrees of Different Structure for the PDT.

An important assumption in the foregoing is that the T is asymptotically normal with mean 0 and variance 1 under the null hypothesis of no linkage disequilibrium. The difficulty that can be encountered is that for some cases the expected value of T may actually be different from 0 under the null hypothesis, which results in an inflated type I error. This is best illustrated by an example. Consider a fully penetrant dominant disease locus (with alleles $d_1$ and $d_2$) with no phenocopies, so that there is probability 1 that an individual with at least one copy of the disease allele is affected. Further assume that the disease allele ($d_1$) is rare so that in any pedigree, there is at most one copy of the disease allele segregating. Suppose that we have sampled extended three-generation pedigrees with the structure shown in FIG. 3. Only families in which the grandparent (GP2), parent (P2) and offspring (O) are all affected can lead to bias. Otherwise there will be at most one informative triad. Disease locus genotypes are fully specified given the affection status (see FIG. 3).

Figure 3:
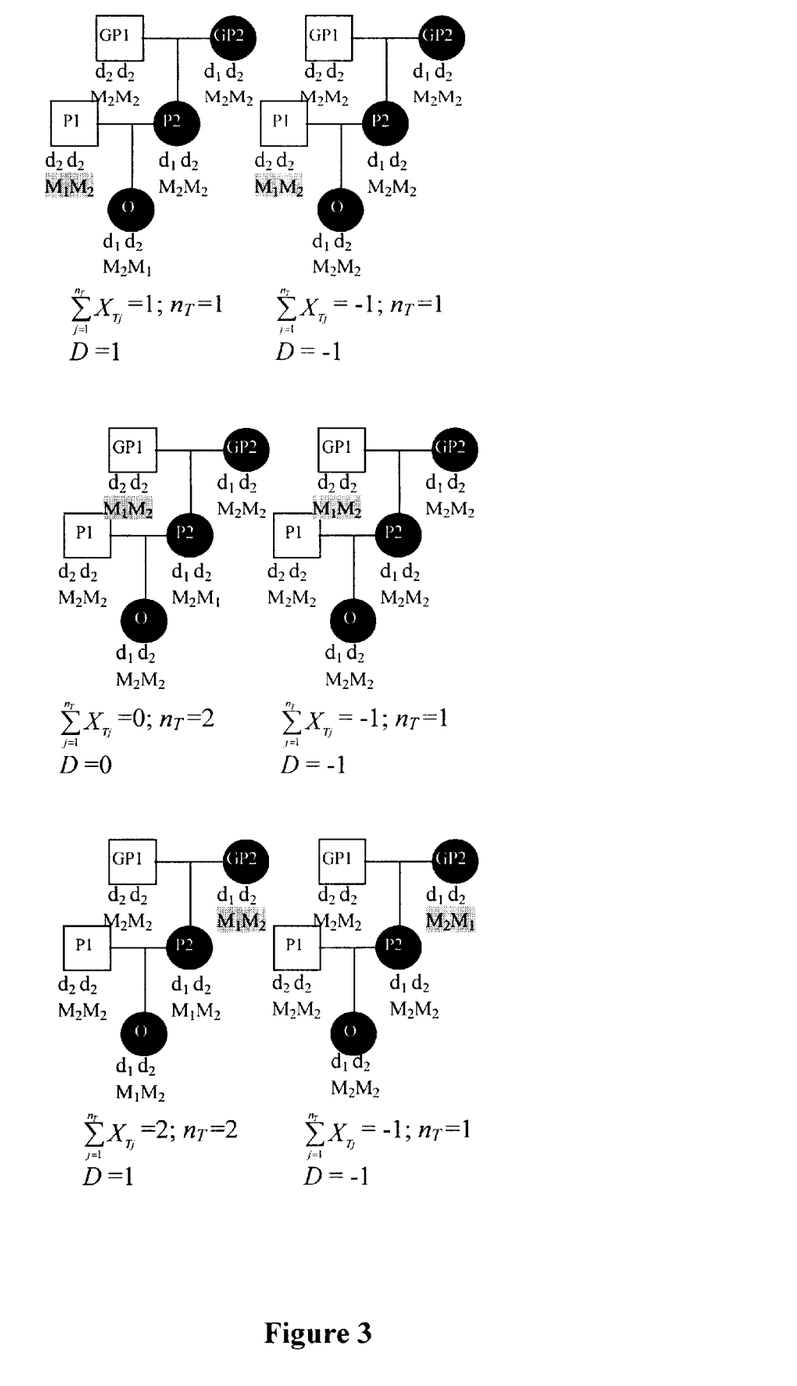
FIG. 3. Pedigrees illustrating PDT bias. Filled in shapes indicate affected individuals and unfilled shapes indicate unaffected individuals. Disease locus and marker locus genotypes are shown for each individual. Values of quantities from equation 1 are given for each pedigree.

Suppose that there is a marker locus fully linked to the disease locus (no recombination), but that there is no allelic association between the alleles at the two loci. This is the null hypothesis for the PDT. Further suppose that the marker locus has two alleles with one allele, say $M_1$, being rare so that only one founder is heterozygous at the marker (families with no heterozygotes are not informative and so are not considered), and any of the three founders (GP1, GP2 or P1) are equally likely to be the heterozygote. The possible transmission patterns and calculation of relevant quantities are shown in FIG. 3. For each we give the value of D, $X_T$ and $n_T$. Each of the 6 pedigrees in FIG. 3 is equally likely under the null hypothesis for the model given. Taking the expectation of D over these pedigrees yields $E(D)=-\frac{1}{6}$. So in this example, it is not the case that $E(T)=0$.

From this example we can see that the problem is that when a grandparent is heterozygous, even though they are equally likely to transmit $M_1$ or $M_2$, the weights in the average differ depending on which allele is transmitted. If $M_1$ is transmitted, then the average is over $n_T=2$. If $M_2$ is transmitted, then the average is over $n_T=1$. Thus, there is a bias toward saying that the more common allele is transmitted more often, even under the null hypothesis of equal transmission.

One can construct an unbiased test by requiring that the weights used in the average be independent of marker genotype. One alternative (PDT-avg) is to average over all phenotypically informative units. Specifically, let $n_T$ be the number of fully genotyped family triads, irrespective of heterozygosity, and let $n_S$ be the number of DSPs without requiring them come from an informative sibship. For the example in FIG. 3, PDT-avg is calculated setting all $n_T=2$ and this gives $E(D)=0$. A second alternative (PDT-sum) is to use the sum from (1) and not average at all. This also give $E(D)=0$ for the example in FIG. 1 since all $n_T=1$ for PDT-sum. Approaches also based on sums of random variables within pedigrees have been proposed by others (G. Abecasis et al., *Genetics* 8, 545–551 (2000); D. Rabinowitz and N. Laird, *Human Heredity* 50, 211–223 (2000); J. Teng and N. Risch, *Genome Research* 9, 234–241 (1999)). Intuitively, basing a statistic on the sum gives more weight to families with more phenotypically informative units, while averaging gives all families equal weight.

To compare these alternative tests to the original form of the PDT (PDT-old), we estimated Type I error and power for the tests using simulations (Table 6). The same genetic models (1–6) from above were used in these simulations and marker and disease allele frequencies were 0.3. To simulate the null, we simulated no allelic association between the marker and disease loci, but did not allow recombination.

For each estimate 5000 replicate samples of 250 extended pedigrees of the structure used above were simulated. These simulations differ from those shown above. Previously, ascertainment was assumed to be random with respect to affection status. In an attempt to more realistically simulate ascertainment of extended pedigrees, the current simulations produce pedigrees conditional on having at least one affected cousin pair.

The results show that for the cases examined all tests have type I error close to the nominal level of 0.05, thus are valid for these models. As we found above, there is little bias reflected in the test using the original form of the statistic, though the estimates of Type I error are larger than those for PDT-avg and PDT-sum for each model. Part of the reason that there is little bias in these simulations was our choice of allele frequency for the marker. It can be shown that there is no bias when the frequencies of the marker alleles are 0.5. In these simulations, we used frequencies of 0.3 and 0.7 so there was less bias than expected for cases with more extreme allele frequencies. An additional reason that little bias was seen is that we did not use grandparental genotypes in the calculation of the test statistic. It is possible to show that when there are only two generations in the pedigree, there will be little bias as long as the genetic effect is not large. In these simulations, the genetic effect was low (i.e., the penetrances are all similar) for each of the models considered. It is noteworthy that if grandparental genotypes were used, there could be a bias even if there is no genetic effect due to this locus (i.e., equal penetrances).

The results in Table 6 demonstrate that the new tests can be more powerful than the original test. For these simulations, we found that power is similar for PDT-avg and PDT-sum, but this will not always be the case. The PDT-sum gives more weight to families of larger size while PDT-avg gives all families equal weight. Thus, if pedigrees contain a similar number of phenotypically informative family units, then the values of the statistics will be similar. Differences will be most apparent when families are of different sizes. Exploratory simulations (not shown) have demonstrated that in many cases the PDT-sum can be more powerful than PDT-avg; however, neither test is uniformly more powerful over all genetic models.

In summary, we have identified examples in which the original form of the PDT can be biased. There is no bias when using the original form of the statistic in nuclear families (with or without parents) or when the marker allele frequencies are 0.5. The bias is evident only when there are multiple generations contributing to the statistic, when the genetic effect for the locus is strong and when marker-allele frequencies are extreme. We have proposed two alternative statistics that not only remove the bias, but also result in tests that can be more powerful than the original test. These tests provide valid alternatives for assessing linkage disequilibrium in general pedigrees.

TABLE 6

Estimates of type I error and power for PDTs for various genetic models based on 5000 replicate simulations. Nominal significance level is 0.05.

| | Type I error | | | Power | | |
|---|---|---|---|---|---|---|
| Model | PDT-old | PDT-avg | PDT-sum | PDT-old | PDT-avg | PDT-sum |
| 1 | 0.052 | 0.048 | 0.046 | 0.956 | 0.978 | 0.982 |
| 2 | 0.052 | 0.052 | 0.052 | 0.780 | 0.847 | 0.856 |

TABLE 6-continued

Estimates of type I error and power for PDTs for various genetic models based on 5000 replicate simulations. Nominal significance level is 0.05.

| | Type I error | | | Power | | |
|---|---|---|---|---|---|---|
| Model | PDT-old | PDT-avg | PDT-sum | PDT-old | PDT-avg | PDT-sum |
| 3 | 0.046 | 0.043 | 0.044 | 0.483 | 0.548 | 0.563 |
| 4 | 0.050 | 0.047 | 0.045 | 0.982 | 0.993 | 0.995 |
| 5 | 0.050 | 0.045 | 0.049 | 0.824 | 0.876 | 0.897 |
| 6 | 0.052 | 0.049 | 0.048 | 0.247 | 0.276 | 0.289 |

*Summary of models ($f_{ij}$ is penetrance for genotype ij):
1 $f_{11} = 0.39$ $f_{12} = 0.33$ $f_{22} = 0.26$;
2 $f_{11} = 0.37$ $f_{12} = 0.32$ $f_{22} = 0.27$;
3 $f_{11} = 0.35$ $f_{12} = 0.15$ $f_{22} = 0.28$;
4 $f_{11} = 0.22$ $f_{12} = 0.17$ $f_{22} = 0.12$;
5 $f_{11} = 0.20$ $f_{12} = 0.165$ $f_{22} = 0.13$;
6 $f_{11} = 0.17$ $f_{12} = 0.155$ $f_{22} = 0.14$.

The foregoing is illustrative of the present invention, and is not to be construed as limiting thereof. The invention is defined by the following claims, with equivalents of the claims to be included therein.

That which is claimed is:

1. A method for the analysis of linkage disequilibrium between at least one marker locus and a disease or trait locus of interest, comprising the steps of:
    (a) providing a data set comprising a marker locus with at least two alleles for a plurality of extended pedigrees, where N is the number of unrelated extended pedigrees, at least one of said extended pedigrees containing at least one informative nuclear family or informative discordant sibship; then
    (b) determining a random variable $X_T$ for each triad within an informative nuclear family for each allele $M_i$;
    (c) determining a random variable $X_S$ for each DSP within an informative discordant sibship for each allele $M_i$;
    (d) determining a summary random variable D from $X_S$ and $X_T$ for each of said extended pedigrees for each allele $M_i$, and then;
    (e) determining a statistic T from each of said summary random variables D from each of said N unrelated extended pedigrees for each allele $M_i$ an extreme value for T indicating greater linkage disequilibrium.

2. The method according to claim 1, each of said extended pedigrees containing at least one informative nuclear family.

3. The method according to claim 1, each of said extended pedigrees containing at least one informative discordant sibship.

4. The method according to claim 1, each of said extended pedigrees containing at least one informative nuclear family and at least one informative discordant sibship.

5. The method according to claim 1, wherein said step (b) of determining a random variable $X_T$ for each triad within an informative nuclear family for each allele $M_i$ is carried out according to the formula:

$$X_T = (\text{Number } M_i \text{ transmitted} - \text{Number of } M_i \text{ not transmitted}).$$

6. The method according to claim 1, wherein said step (c) of determining a random variable $X_S$ for each DSP within an informative discordant sibship for each allele $M_i$ is carried out according to the formula:

$$X_S = (\text{Number } M_i \text{ in affected sib} - \text{Number of } M_i \text{ in unaffected sib}).$$

7. The method according to claim 1, wherein each of said extended pedigrees contains $n_T$ triads from informative nuclear families and $n_S$ DSPs from informative discordant sibships, and said step (d) of determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right].$$

8. The method according to claim 1, wherein said step (e) of determining a statistic T from each of said summary random variables D from each of said N unrelated extended pedigrees for each allele $M_i$ is carried out according to formula (1):

$$T = \frac{\sum_{i=1}^{N} D_i}{\sqrt{\sum_{i=1}^{N} D_i^2}} \quad (1)$$

wherein T is a disequilibrium statistic for allele $M_i$, an extreme value for T indicating greater linkage disequilibrium.

9. The method according to claim 1, further comprising the step of:
(f) determining a global statistic T' from each statistic T for each allele $M_i$, an extreme value for T' indicating greater linkage disequilibrium.

10. A method according to claim 1, wherein said extended pedigrees are animal pedigrees.

11. A method according to claim 1, wherein said extended pedigrees are plant pedigrees.

12. A system for the analysis of linkage disequilibrium, comprising:
(a) means for inputting a data set comprising a marker locus with at least two alleles for a plurality of extended pedigrees, where N is the number of unrelated extended pedigrees, at least one of said extended pedigrees containing at least one informative nuclear family or informative discordant sibship; then
(b) means for determining a random variable $X_T$ for each triad within an informative nuclear family for each allele $M_i$;
(c) means for determining a random variable $X_S$ for each DSP within an informative discordant sibship for each allele $M_i$;
(d) means for determining a summary random variable D from $X_S$ and $X_T$ for each of said extended pedigrees for each allele $M_i$; and
(e) means for determining a statistic T from each of said summary random variables D from each of said N unrelated extended pedigrees for each allele $M_i$ an extreme value for T indicating greater linkage disequilibrium.

13. The system according to claim 12, each of said extended pedigrees containing at least one informative nuclear family.

14. The system according to claim 12, each of said extended pedigrees containing at least one informative discordant sibship.

15. The system according to claim 12, each of said extended pedigrees containing at least one informative nuclear family and at least one informative discordant sibship.

16. The system according to claim 12, wherein said means (b) for determining a random variable $X_T$ for each triad within an informative nuclear family for each allele $M_i$ is carried out according to the formula:

$X_T$=(Number $M_i$ transmitted−Number of $M_i$ not transmitted).

17. The system according to claim 12, wherein said means (c) for determining a random variable $X_S$ for each DSP within an informative discordant sibship for each allele $M_i$ is carried out according to the formula:

$X_S$=(Number $M_i$ in affected sib−Number of $M_i$ in unaffected sib).

18. The system according to claim 12, wherein each of said extended pedigrees contains $n_T$ triads from informative nuclear families and $n_S$ DSPs from informative discordant sibships, and said means (d) for determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right].$$

19. The system according to claim 12, wherein said means (e) for determining a statistic T from each of said summary random variables D from each of said N unrelated extended pedigrees for each allele $M_i$ is carried out according to formula (1):

$$T = \frac{\sum_{i=1}^{N} D_i}{\sqrt{\sum_{i=1}^{N} D_i^2}} \quad (1)$$

wherein T is a disequilibrium statistic for allele $M_i$, an extreme value for T indicating greater linkage disequilibrium.

20. The system according to claim 12, further comprising:
(f) means for determining a global statistic T' from each statistic T for each allele $M_i$, an extreme value for T' indicating greater linkage disequilibrium.

21. A computer program product for the analysis of linkage disequilibrium, said computer program product comprising a computer usable storage medium having computer readable program code means embodied in the medium, the computer readable program code means comprising:
(a) computer readable program code means for inputting a data set comprising a marker locus with at least two alleles for a plurality of extended pedigrees, where N is the number of unrelated extended pedigrees, at least one of said extended pedigrees containing at least one informative nuclear family or informative discordant sibship; then
(b) computer readable program code means for determining a random variable $X_T$ for each triad within an informative nuclear family for each allele $M_i$;
(c) computer readable program code means for determining a random variable $X_S$ for each DSP within an informative discordant sibship for each allele $M_i$;
(d) computer readable program code means for determining a summary random variable D from $X_S$ and $X_T$ for each of said extended pedigrees for each allele $M_i$; and (e) computer readable program code means for determining a statistic T from each of said summary random variables D from each of said N unrelated extended pedigrees for each allele $M_i$ an extreme value for T indicating greater linkage disequilibrium.

22. The computer program product according to claim 21, each of said extended pedigrees containing at least one informative nuclear family.

23. The computer program product according to claim 21, each of said extended pedigrees containing at least one informative discordant sibship.

24. The computer program product according to claim 21, each of said extended pedigrees containing at least one informative nuclear family and at least one informative discordant sibship.

25. The computer program product according to claim 21, wherein said means (b) for determining a random variable $X_T$ for each triad within an informative nuclear family for each allele $M_i$ is carried out according to the formula:

$$X_T = (\text{Number } M_i \text{ transmitted} - \text{Number of } M_i \text{ not transmitted}).$$

26. The computer program product according to claim 21, wherein said means (c) for determining a random variable $X_S$ for each DSP within an informative discordant sibship for each allele $M_i$ is carried out according to the formula:

$$X_S = (\text{Number } M_i \text{ in affected sib} - \text{Number of } M_i \text{ in unaffected sib}).$$

27. The computer program product according to claim 21, wherein each of said extended pedigrees contains $n_T$ triads from informative nuclear families and $n_S$ DSPs from informative discordant sibships, and said means (d) for determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right].$$

28. The computer program product according to claim 21, wherein said means (e) for determining a statistic T from each of said summary random variables D from each of said N unrelated extended pedigrees for each allele $M_i$ is carried out according to formula (1):

$$T = \frac{\sum_{i=1}^{N} D_i}{\sqrt{\sum_{i=1}^{N} D_i^2}} \quad (1)$$

wherein T is a disequilibrium statistic for allele $M_i$, an extreme value for T indicating greater linkage disequilibrium.

29. The computer program product according to claim 21, further comprising:

(f) computer readable program code means for determining a global statistic T' from each statistic T for each allele $M_i$, an extreme value for T' indicating greater linkage disequilibrium.

30. The method according to claim 1, wherein each of said extended pedigrees contains $n_T$ triads from informative nuclear families and $n_S$ DSPs from informative discordant sibships, and said step (d) of determining a summary random variable D from $X_S$ and $X_T$ for each of said extended pedigrees for each allele $M_i$ is carried out according to the formula:

$$D = \sum_{j=1}^{n_T} X_{Tj} + \sum_{j=1}^{n_S} X_{Sj}.$$

31. A method according to claim 30, wherein said $n_T$ triads from informative nuclear families and $n_S$ DSPs from informative discordant sibships are selected based upon a criteria other than genotype.

32. The method according to claim 1, wherein each of said extended pedigrees contains $n_T$ triads from nuclear families and $n_S$ DSPs from discordant sibships, and said step (d) of determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right].$$

wherein said $n_T$ triads from nuclear families and $n_S$ DSPs from discordant sibships are selected based upon a criteria other than genotype.

33. A method according to claim 32, wherein said criteria other than genotype is selected from the group consisting of age, gender, clinical characteristic, phenotype, and random.

34. A method according to claim 32, wherein each of said extended pedigrees contains $n_T$ triads from the total number of nuclear families and $n_S$ DSPs from the total number of discordant sibships.

35. The system according to claim 12, wherein each of said extended pedigrees contains $n_T$ triads from informative nuclear families and $n_S$ DSPs from informative discordant sibships, and said step (d) of determining a summary random variable D from $X_S$ and $X_T$ for each of said extended pedigrees for each allele $M_i$ is carried out according to the formula:

$$D = \sum_{j=1}^{n_T} X_{Tj} + \sum_{j=1}^{n_S} X_{Sj}.$$

36. The system according to claim 35, wherein said $n_T$ triads from informative nuclear families and $n_S$ DSPs from informative discordant sibships are selected based upon a criteria other than genotype.

37. The system according to claim 12, wherein each of said extended pedigrees contains $n_T$ triads from nuclear families and $n_S$ DSPs from discordant sibships, and said step (d) of determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right]$$

wherein said $n_T$ triads from nuclear families and $n_S$ DSPs from discordant sibships are selected based upon a criteria other than genotype.

38. The system according to claim 37, wherein said criteria other than genotype is selected from the group consisting of age, gender, clinical characteristic, phenotype, and random.

39. The system according to claim 37, wherein each of said extended pedigrees contains $n_T$ triads from the total number of nuclear families and $n_S$ DSPs from the total number of discordant sibships.

40. The computer program product according to claim 27, wherein each of said extended pedigrees contains $n_T$ triads from informative nuclear families and $n_S$ DSPs from informative discordant sibships, and said step (d) of determining a summary random variable D from $X_S$ and $X_T$ for each of said extended pedigrees for each allele $M_i$ is carried out according to the formula:

$$D = \sum_{j=1}^{n_T} X_{Tj} + \sum_{j=1}^{n_S} X_{Sj}.$$

41. The computer program product according to claim 40, wherein said $n_T$ triads from informative nuclear families and $n_S$ DSPs from informative discordant sibships are selected based upon a criteria other than genotype.

42. The computer program product according to claim 40, wherein each of said extended pedigrees contains $n_T$ triads from nuclear families and $n_S$ DSPs from discordant sibships, and said step (d) of determining a summary random variable D from $X_S$ and $X_T$ for each of said extended pedigrees for each allele $M_i$ is carried out according to the formula:

$$D = \frac{1}{n_T + n_S}\left[\sum_{j=1}^{n_T} X_{Tj} + \sum_{j=1}^{n_S} X_{Sj}\right]$$

wherein said $n_T$ triads from nuclear families and $n_S$ DSPs from discordant sibships are selected based upon a criteria other than genotype.

43. The computer program product according to claim 42, wherein said criteria other than genotype is selected from the group consisting of age, gender, clinical characteristic, phenotype, and random.

44. The computer program product according to claim 42, wherein each of said extended pedigrees contains $n_T$ triads from the total number of nuclear families and $n_S$ DSPs from the total number of informative sibships.

* * * * *